United States Patent [19]

Ampleman

[11] Patent Number: 5,256,804

[45] Date of Patent: Oct. 26, 1993

[54] GLYCIDYL AZIDE POLYMER

[75] Inventor: Guy Ampleman, St-Augustin de Desmaures, Canada

[73] Assignee: Her Majesty the Queen as represented by the Ministry of National Defence of Her Majesty's Canadian Government, Ottawa, Canada

[21] Appl. No.: 955,995

[22] Filed: Oct. 2, 1992

[30] Foreign Application Priority Data

Oct. 3, 1991 [CA] Canada .................................. 2052728

[51] Int. Cl.$^5$ .......................................... C07C 247/04
[52] U.S. Cl. ......................................... 552/10; 552/1; 552/11
[58] Field of Search ............................. 552/1, 10, 11

[56] References Cited

U.S. PATENT DOCUMENTS

| | | | |
|---|---|---|---|
| 4,925,909 | 5/1990 | Kubota et al. | 552/11 |
| 4,937,361 | 7/1990 | Wagner et al. | 552/11 |
| 5,055,600 | 10/1991 | Wagner | 552/11 |
| 5,124,463 | 7/1992 | Ampleman | 552/11 |

Primary Examiner—Marianne M. Cintins
Assistant Examiner—Kimberly J. Kestler
Attorney, Agent, or Firm—Nixon & Vanderhye

[57] ABSTRACT

Glycidyl azide polymers, which are used as binders in composite explosive and propellant compositions, include hydroxyl groups which react with the isocyanate curing agent normally used in such compositions. Since the functionality of available linear glycidyl azide polymers is less than two, triols and/or triisocyanates are needed to crosslink the chains to form a matrix. A glycidyl azide polymer with increased functionality (higher than two) and reactivity obviates the need for triols and triisocyanates in the compositions. Moreover, a glycidyl azide polymer with primary hydroxyl groups would give faster curing reactions at lower temperatures without gassing problems, eliminating the need for a catalyst. Examples of glycidyl azide polymer having increased functionality have one of the formulae:

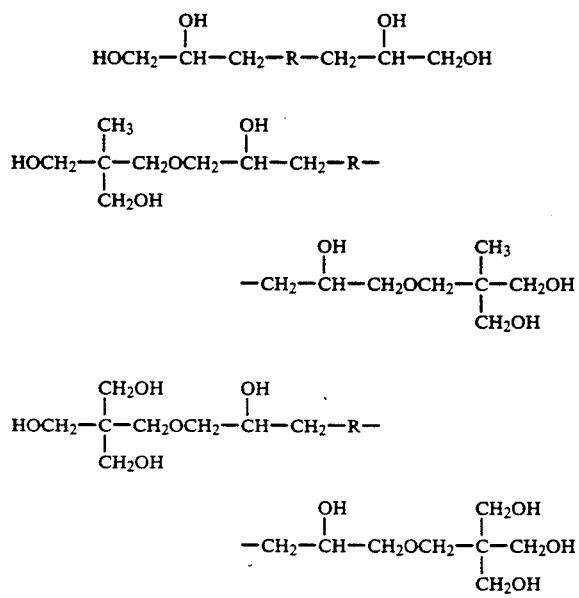

wherein R is

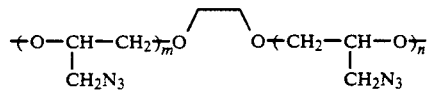

wherein m and n are different from zero, and m+n is 4 to 60.

4 Claims, No Drawings

GLYCIDYL AZIDE POLYMER

This invention relates to a linear glycidyl azide polymer, and to a process for preparing such a polymer.

In particular, the invention relates to the synthesis of an innovative class of glycidyl azide polymers (GAP) having a linear structure combined with an increased funcitonality, on to the polymers thus produced.

High energy solid compositions such as propellants, composite explosives or the like include an elastomeric binder with particulate solids such as oxidizers, particulate fuel material and crystalline explosives dispersed therein. Glycidyl azide polymer (GAP) serves as an energetic binder to form a matrix for ammonium nitrate in new insensitive low smoke propellant formulations and for RDX in new insensitive composite explosives.

Since the functionality of available glycidyl azide polymers is less than two, many additives must be added to the formulation to ensure good curing and better mechanical properties. For example, to increase reticulation and to form a good matrix, triol or triisocyanate or both must be used to crosslink polymer chains.

Moreover, hydroxyl groups of glycidyl azide polymer are secondary which represents a problem. In fact, the reactivity of the terminal secondary hydroxyl groups in linear glycidyl azide polymers is equal to the reactivity of water towards isocyanate. Therefore, water can react with the isocyanate in the curing reaction causing gas evolution which results in cracks and bubbles in the cured propellants In order to overcome the problem, a vacuum can be applied and/or catalysts can be used to increase the reactivity of the secondary hydroxyl groups with the isocyanate. Thus, variable parameters are introduced into the system. Such variable parameters, especially those used to increase reticulation, make it difficult to achieve reproducibility from batch to batch.

It is highly desirable to have a glycidyl azide polymer with increased functionality (higher than two) and reactivity, because crosslinking agents such as triols or triisocyanates would no longer be necessary. Thus, the variable parameters could be reduced in the system. Moreover, a glycidyl azide polymer with primary hydroxyl groups would give faster curing reactions at lower temperatures without gassing problems, eliminating another variable, namely the need for a catalyst. Without such a catalyst, the system would be easier to control and reproducible propellant formulations could be obtained.

The object of the present invention is to meet the above defined need by providing a linear glycidyl azide polymer with increased functionality, and a process for producing such a polymer.

According to one aspect, the present invention relates to a process for preparing a linear glycidyl azide polymer comprising the steps of epoxidizing polyepichlorohydrin; opening the resulting epoxide; and azidizing the thus produced polymer with an alkali metal azide.

According to a second aspect, the invention relates to a linear glycidyl azide polymer of the formula:

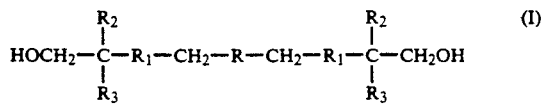

where R is

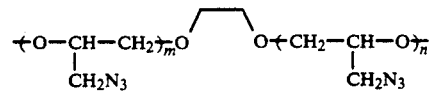

wherein m and n are different from zero, and m+n is 4 to 60, $R_1$ is a single bond and the group —$CH_2OCH_2$—CHOH—; when $R_1$ is a single bond, $R_2$ is a hydroxyl group and $R_3$ is hydrogen, and when $R_1$ is the group —$CH_2OCH_2$—CHOH—, $R_2$ is $CH_3$ or $CH_2OH$ and $R_3$ is $CH_2OH$.

Polyepichlorohydrin of different molecular weights is commercially available. In general, any polyepichlorohydrin having a molecular weight (Mw) of 500 to 6000 can be used in the process described herein. In the following example, polyepichlorohydrin having a molecular weight of 2000 is described.

Polyepichlorohydrins have the general formula:

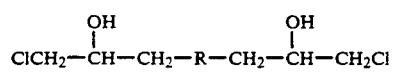

wherein R is:

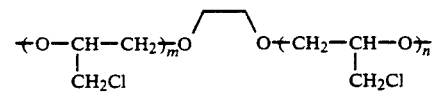

m and n are different from zero and m+n can vary from 4 to 60.

The epoxidation is highly regiospecific and occurs only at the ends of the polymer to yield oxirane rings as confirmed by NMR analyses. In the presence of hydrides or bases, epoxidation occurs in the following manner:

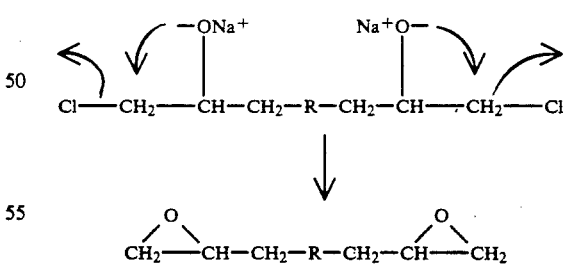

The following examples describe a typical three-stage process.

EXAMPLE 1

EPOXIDATION 50 g of polyepichlorohydrin (PECH) is added to 500 mL of dry tetrahydrofuran in a 1000 mL three neck flask equipped with a reflux condenser and surmounted by an anhydrous calcium chloride tube under a dry nitrogen atmosphere. The solution is stirred and gently warmed until dissolution of the PECH. 5.33 g (0.22 mole) of sodium hydride is added, and the solution is heated to reflux for twenty-four hours. After cooling, water (100 mL) is added and tetrahydrofuran is evaporated. The mixture is extracted three times with methylene chloride (100 mL). The combined organic phases are washed with water (3×100 mL), washed with brine (2×100 mL) and dried over magnesium sulfate, filtered and evaporated to dryness yielding the epoxide (48 g, quantitative).

The infrared and nuclear magnetic resonance analyses of the product are as follows: IR: $\nu_{max}$(NaCl)cm$^{-1}$: 3020–2880, 1475–1430, 1350, 1320, 1260, 1200, 1120, 920, 850, 760, 710.

$^1$H NMR: $\delta$ (CDCl$_3$) ppm: 2.59 (1 H, one of CH$_2$ epoxide, ddt; $^2J=4.4$ Hz, $^3J=7.0$ Hz, $^4J=0.9$ Hz) 2.78 (1 H, the other H of CH$_2$ epoxide, tt; $^2J=4.5$ Hz, $^3J=4.5$ Hz, $^4J=0.7$ Hz) 3.14 (1 H, CH epoxide, m), 3.5–3.9 (all other protons, m).

$^{13}$C NMR: $\delta$ (CDCl$_3$) ppm: 43.4 (CH$_2$Cl) 44.0 (CH$_2$-epoxide), 50.8 (CH-epoxide), 69.0–71.5 (CH$_2$O), 78.1 (CHO).

Note: In the spectra analyses, IR=infrared, $^1$H NMR=proton nuclear magnetic resonance, $^{13}$C NMR=carbon nuclear magnetic resonance, j=coupling constant in hertz(H$_z$), m=multiplet, s=singlet, d=doublet, t=triplet.

Sodium hydride can be replaced by crushed potassium hydroxide in this step of the process. Therefore the presence of water is less critical and drying precautions can be avoided, giving an easier and less expensive step.

At this point of the precess, two routes can be taken. The functionality can be increased by simply opening the epoxide with water under acidic conditions leading to a polymer with a functionality increased by a factor two or, by reacting the epoxide with a triol or a tetraol in absence of water to lead to a functionality increased by a factor three or four respectively.

The results of the analyses of this product are as follows:
IR: $\nu_{max}$ (NaCl) cm$^{-1}$: 3650–3250, 3020–2880, 1475–1430, 1350, 1310, 1260, 1200, 1100, 900, 850, 760, 710.

$^1$H HMR: $\delta$ (CDCl$_3$) ppm: 3.9–3.5 (m, all protons).

$^{13}$C NMR: $\delta$ (CDCl$_3$) ppm: 43.63 (CH$_2$Cl), 62.40–63.64 (CH$_2$OH), 69.37–71.37 (CH$_2$O), 78.60–78.96 (CHO,CHOH).

The epoxidation of Example 1 and the epoxide opening of Example 2 can be done successively in a one-pot synthesis. Following epoxidation, neutralization of the potassium hydroxide with sulfuric acid leaves substantial quantities of acidic water which is required for the hydrolysis of the epoxide. Thus, the desired product can be obtained without isolating the epoxide. If azidation is considered as a second step, a glycidyl azide polymer with its functionality doubled is obtained in a two-step process from PECH.

EXAMPLE 3

TRIPLING FUNCTIONALITY

In order to increase the functionality by a factor of three, a triol such as tris-1,1,1-hydroxymethyl ethane is used.

10 g of epoxide terminated polyepichlorohydrin is added to 200 mL of N,N-dimethylformamide (previously dried over a molecular sieve for 24 hours) in a 500 mL three neck flask equipped with a reflux condenser and surmounted by an anhydrous calcium chloride tube. After dissolution of the polymer, 3.3 g (0.03 MOLE) of tris-1,1,1-hydroxymethyl ethane is added and the solution is heated to 140° C. for 24 hours. After cooling, the DMF is evaporated under vacuum. Methylene chloride (100 mL) is added to dissolve the polymer, the insoluble triol is removed by filtration and the organic solvent is evaporated to yield 10.5 g, (96%) of the polymer. The structure of the product is as follows:

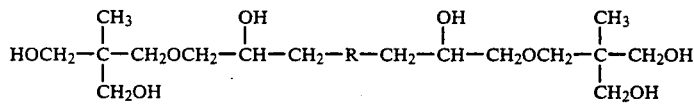

EXAMPLE 2

DOUBLING FUNCTIONALITY 10 g of the epoxide-terminated (PECH) previously prepared is added to 200 mL of tetrahydrofuran in a 500 mL three neck flask equipped with a reflux condenser. Water (5 mL) is added, followed by addition of concentrated sulfuric acid (2 drops) and the solution is heated to reflux overnight. Water (50 mL) is added and tetrahydrofuran is evaporated. The aqueous phase is extracted three times with methylene chloride (50 mL). The organic phase is washed with water (3×50 mL), then with brine (2×50 mL) and dried over magnesium sulfate, filtered and evaporated to yield a polymer (8.87 g, 88%) with the following structure:

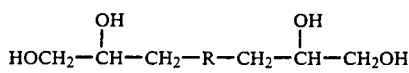

the results of the analyses of this product are as follows:
IR: $\nu_{max}$ (NaCl) cm$^{-1}$: 3500–3300, 3020–2880, 1475–1430, 1390, 1305, 1260, 1220, 1100, 910, 750.

$^1$H NMR: $\delta$ (CDCl$_3$) ppm: 3.9–3.5 (m, all other protons), 0.9–0.8 (s, 3H,CH$_3$).

$^{13}$C NMR: $\delta$ (CDCl$_3$) ppm: 16.80 (CH$_3$), 43.69 (CH$_2$Cl), 62.66–65.62 (CH$_2$OH), 69.32–71.33 (CH$_2$), 78.91 (CHO,CHOH).

EXAMPLE 4

QUADRUPLING FUNCTIONALITY

In order to increase the functionality by a factor of four, a tetraol is used. This example is performed in the same manner as Example 3, except that the tris-1,1,1-hydroxymethyl ethane is replaced with pentaerythrytol to produce a polymer of the following structure.

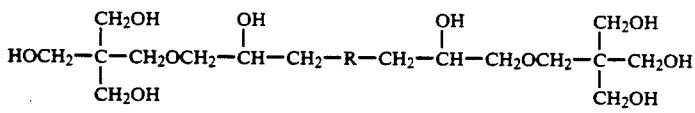

The results of the analyses of this polymer are as follows:

IR: $\nu_{max}$ (NaCl) cm$^{-1}$: 3500–3300, 3040–2880, 1480–1430, 1390, 1350, 1305, 1260, 1200, 1100, 900, 740.

$^1$H NMR: $\delta$ (CDCl$_3$) ppm: 3.8–3.5 (m, all protons).

$^{13}$C NMR: $\delta$ (CDCl$_3$) ppm: 43.67 (CH$_2$Cl), 61.78–62.80 (CH$_2$OH), 69.34–71.34 (CH$_2$O), 78.93 (CHO,CHOH).

In order to produce a glycidyl azide polymer with increased functionality, azidation of the polymer of Example 2, 3 or 4 must be effected. Azide groups replace the chloride groups along the complete length of the chain to produce polymers where R is as follows:

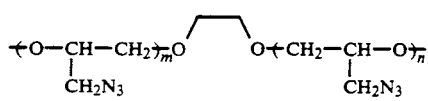

An example of the azidation follows.

EXAMPLE 5

AZIDATION

The PECH from Example 2, 3 or 4 is dissolved in DMF in a three neck flask equipped with a reflux condenser, and the solution is heated at 85° C. Sodium azide is then added slowly and the solution is heated at 100° C. and stirred for 48 hours. After cooling, the mixture is filtered and the DMF is evaporated under vacuum. Water and methylene chloride is added and separated. The organic layer is washed three times with water followed by a final wash with brine. The organic phase is dried over magnesium sulfate, filtered and evaporated to yield the corresponding glycidyl azide polymer (70–88%). All results of the analyses of the GAPs reveals and confirms structures previously proposed by IR and NMR. IR spectra show strong absorption band at 2100 cm$^{-1}$ corresponding to azide groups. $^{13}$CNMR spectra show signals at 52 ppm and absence of signals at 43 ppm indicating that azidation has been completed.

It should be noted that when using triol or tetraol to open epoxide as in Examples 3 and 4, the epoxide opening and the azidation could be done successively in the same pot. After epoxide opened at 140° C., the solution is cooled to 85° C., sodium azides added and the solution is heated at 100° C. The reaction runs for 48 hours affording a one-pot synthesis for these two steps. Thus, a two-step process is available for both methods of opening, namely epoxide opening with water or with alcohols. When water is involved, epoxidation followed by opening is done in THF in a first step; and the second step is azidation in DMF. When triol or tetraol are involved, epoxidation in THF is done as first step; and the second step is epoxide opening followed by azidation in DMF.

SUMMARY

In the new process described above, epoxidation is a regiospecific reaction, and the epoxide terminated PECH is a very useful product, because it provides a regiospecific means for introducing new groups on both ends of the polymer. Introduction of water or alcohols (triol or tetraol) has been achieved to increase functionality.

The embodiments of the invention in which an exclusive property or privilege is claimed are defined as follows:

1. A linear glycidyl azide polymer of the formula

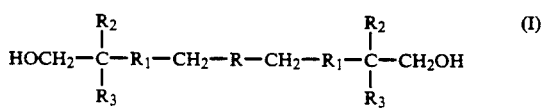

where R is

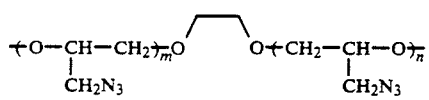

wherein m and n are different from zero, and m+n is 4 to 60, R$_1$ is a single bond or the group —CH$_2$OCH$_2$—CHOH—; when R$_1$ is a single bond, R$_2$ is a hydroxyl group and R$_3$ is hydrogen, and when R$_1$ is the group —CH$_2$OCH$_2$—CHOH—, R$_2$ is CH$_3$ or CH$_2$OH and R$_3$ is CH$_2$OH.

2. A linear glycidyl azide polymer of the formula:

HOCH$_2$—CH(OH)—CH$_2$—R—CH$_2$—CH(OH)—CH$_2$OH wherein R is

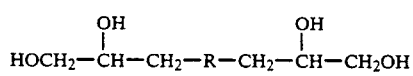

m and n are different from zero, and m+n is 4 to 60.

3. A linear glycidyl azide polymer of the formula:

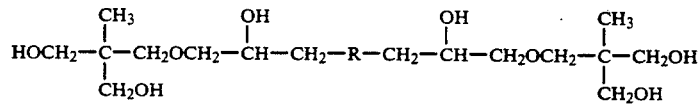

wherein R is

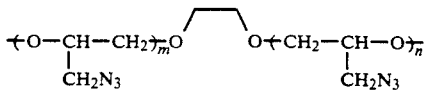

m and n are different from zero, and m+n is 4 to 60.

4. A linear glycidyl azide polymer of the formula:

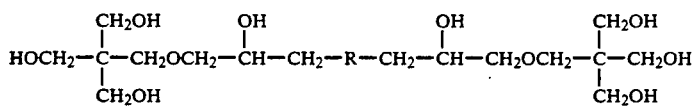
wherein R is
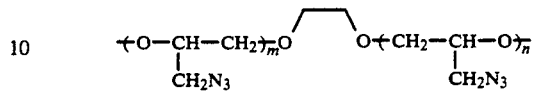
m and n are different from zero, and m+n is 4 to 60.
* * * * *

UNITED STATES PATENT AND TRADEMARK OFFICE
CERTIFICATE OF CORRECTION

PATENT NO. : 5,256,804
DATED : October 26, 1993
INVENTOR(S) : Ampleman

It is certified that error appears in the above-indentified patent and that said Letters Patent is hereby corrected as shown below:

Column 1 line 9, delete "funcitonality" and replace by --functionality--.

Column 2 line 1, delete the formula (I) and replace by the new formula (I) shown below.

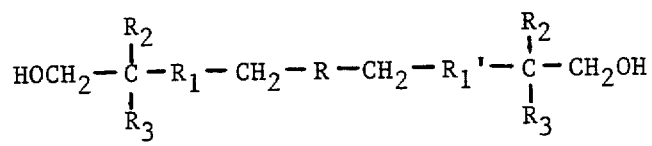

Column 2 line 16, delete "bond and" and replace by --bond or--.

Column 2 line 17, insert --, $R_1'$ is a single bond or the group $CHOH-CH_2OCH_2-$ -- after "-CHOH-".

Column 3 line 32, delete "precess" and replace by --process--.

UNITED STATES PATENT AND TRADEMARK OFFICE
CERTIFICATE OF CORRECTION

PATENT NO. : 5,256,804
DATED : October 26, 1993
INVENTOR(S) : Ampleman

It is certified that error appears in the above-indentified patent and that said Letters Patent is hereby corrected as shown below:

Column 6 line 23, delete the formula (I) and replace by the following:

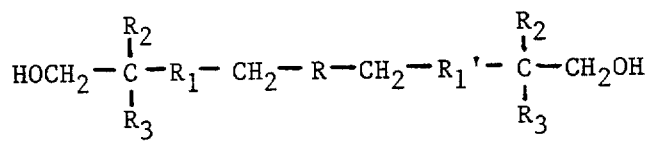

Column 6 line 35, insert --, $R_1'$ is a single bond or the group -CHOH-CH$_2$OCH$_2$- -- after "CHOH-".

Column 6 line 35, delete "when $R_1$ is" and replace by --when $R_1$ and $R_1'$ are--.

Column 6 line 37, insert --and $R_1'$ is the group CHOH-CH$_2$OCH$_2$- -- after "CHOH-".

Signed and Sealed this

Twenty-third Day of August, 1994

Attest:

BRUCE LEHMAN

Attesting Officer      Commissioner of Patents and Trademarks